United States Patent [19]

Jessel, Jr. et al.

[11] Plant 4,531

[45] May 6, 1980

[54] CHRYSANTHEMUM PLANT

[75] Inventors: Walter H. Jessel, Jr., Gantsville, W. Va.; William E. Duffett, Salinas, Calif.

[73] Assignee: Yoder Brothers, Inc., Barberton, Ohio

[21] Appl. No.: 963,853

[22] Filed: Nov. 27, 1978

[51] Int. Cl.[2] ..... A01H 5/00

[52] U.S. Cl. ..... Plt./76

[58] Field of Search ..... Plt./76

*Primary Examiner*—Robert E. Bagwill

*Attorney, Agent, or Firm*—Donald D. Jeffery

[57] ABSTRACT

A chrysantheumum cultivar particularly characterized as to uniqueness by the combined characteristics of flat capitulum form, spooned daisy capitulum type, dark lavender pink ray floret color, diameter across face of capitulum up to 10 cm., tall plant height, semi-spreading branching pattern, average natural season flowering date of September 22, and average flowering response period of seven weeks in photoperiodic controlled short day programs.

2 Drawing Figures

The present invention comprises a new and distinct cultivar of *Chrysanthemum morifolium,* Ramat., hereinafter referred to by the cultivar name Lancer.

Lancer is a product of a planned breeding program which had the objective of creating cultivars with spooned daisy capitulum type, tall height, semi-spreading branching pattern, durable inflorescence, short (six to seven week) flowering response period, and lavender ray floret color under outdoor natural season conditions.

Lancer was originated from a cross made in a controlled breeding program in Barberton, Ohio in the year 1975. The male parent was #75017002 (unnamed seedling), a purple spooned single originated by the present inventors from a cross between #7401001 (unnamed seedling) and #74022001 (unnamed seedling). The female parent of Lancer was Liberty (U.S. Plant Pat. No. 3,933). #74010001, #74022001, and Liberty are all products of the breeding program of applicants.

Lancer was discovered and selected as a flowering plant within the progeny of the stated cross by Walter H. Jessel, Jr. and William E. Duffett On Apr. 27, 1976 in a controlled environment in Barberton, Ohio. The first act of asexual reproduction of Lancer was accomplished when vegetative cuttings were taken from the initial selection in June, 1976 in Barberton, Ohio by a technician working under formulations established and supervised by Walter H. Jessel, Jr. and William E. Duffett. Horticultural examination of selected units initiated Sept. 20, 1976 has demonstrated that the combination of characteristics as herein disclosed for Lancer are firmly fixed and are retained through successive generations of asexual reproduction.

Lancer has not been observed under all possible environmental conditions. The phenotype may vary significantly with variations in environment such as temperature, light intensity, and daylength. The following observations, measurements, and comparisons describe plants grown in a field in Barberton, Ohio and Salinas, Calif. under conditions which are generally described in *Local Climatological Data, Annual Summary with Comparative Data, Akron, Ohio,* U.S. Department of Commerce, National Oceanic and Atmospheric Administration, Environmental Data Service, Washington, D.C. 1976 and *Local Climatological Data, Annual Summary with Comparative Data, Salinas, Calif.,* U.S. Department of Commerce, National Oceanic and Atmospheric Administration, Environmental Data Service, Washington, D.C. 1977, 1978.

The following traits have been repeatedly observed and are determined to be basic characteristics of Lancer which in combination distinguish this chrysanthemum as a new and distinct cultivar:

(1) Flat capitulum form.

(2) Spooned daisy capitulum type.

(3) Dark lavender pink ray floret color.

(4) Diameter across face of capitulum up to 10 cm.

(5) Tall plant height (requiring one long day week prior to short days and 1 application of 2500 ppm B9-SP to attain a flowered plant height of 28 to 35 cm.).

(6) Semi-spreading branching pattern.

(7) Average natural season flowering date of September 22.

(8) Average flowering response period of seven weeks in photoperiodic controlled flowering programs.

The accompanying photographic drawings show typical inflorescence and growth characteristics of Lancer. Sheet 1 is a color photograph depicting the inflorescence of Lancer. Some degree of difficulty was encountered in obtaining accurate color representation, with the photographic drawing being slightly more red and less blue than the actual flower color of Lancer. In addition, the more intense coloration of the petal tips did not photograph with the color intensity observed and specified within the application text. The color specifications set forth below are, however, correct. Sheet 2 is a black and white photograph showing typical growth and foliage characteristics of Lancer.

Of the many commercially available cultivars known to the present inventors, the most similar existing cultivar in comparison to Lancer is the parental cultivar Liberty.

Reference is made to attached Chart A which compares certain characteristics of Lancer with the same characteristics of Liberty. It will be noted that in comparison to Liberty, Lancer has darker ray floret color, different capitulum type, later natural season flowering date, more erect branching pattern, and larger diameter across face of inflorescence. The capitulum form and plant height of Lancer are similar to those same characteristics of Liberty.

In the following description, color references are made to A Limit Color Cascade, by the Munsell Company, 1972 edition. The color values were determined between 2:00 and 2:30 P.M. on Sept. 12, 1978 under 125 foot-candle light intensity at Salinas, Calif.

Botanical classification: *Chrysanthemum morifolium,* Ramat., cv Lancer

I. INFLORESCENCE:

A. *Capitulum.*—Form: flat. Type: spooned daisy. Permanence: 14–21 days. Diameter across face: 9 to 10 cm.

B. *Corolla of ray florets.*—Color (outside of tubular petal): 46-6 to 45-6 but more greyed, oxidizing with age to 46-3 to 45-3, but more greyed. Color (inside of flair at petal tip): 46-12 to 45-12, oxidizing to 46-6 to 46-5, but more greyed.

C. *Corolla of disc florets.*—Color: 24-9 to 24-8.

D. *Reproductive organs.*—Androecium: present disc florets; scant pollen. Gynoecium: present both ray and disc florets.

II. PLANT:

A. *General appearance.*—Semi-spreading branching patterns; tall plant height (ranging at flower date from 32 to 36 cm. when planted July 10 as a rooted cutting under outdoor natural season conditions).

B. *Foliage.*—Color (abaxial): approximately 20'-14. Color (adaxial): approximately 20-13 overlaid with white.

CHART A

COMPARISON OF LANCER AND LIBERTY.

| CULTIVAR | RAY FLORET COLOR | CAPITULUM FORM AND TYPE | AVERAGE NATURAL SEASON FLOWER DATE |
|---|---|---|---|
| Lancer | Dark lavender pink | Flat spooned daisy | September 22 |
| Liberty | Lavender pink | Flat spooned anenome | September 18 |

| CULTIVAR | PLANT HEIGHT | BRANCHING PATTERN AND SPREAD | DIAMETER ACROSS FACE OF CAPITULUM |
|---|---|---|---|
| Lancer | Tall, ranging up to 175 mm. | Semi-spreading | 90 to 100 mm. |
| Liberty | Tall, ranging up to 175 mm. | Spreading | 55 to 75 mm. |

COMPARISONS MADE OF PLANTS GROWN UNDER NATURAL SEASON OUTDOOR FIELD CONDITIONS IN BARBERTON, OHIO AND SALINAS, CALIFORNIA.

We claim:

1. A new and distinct cultivar of *Chrysanthemum morifolium,* Ramat. plant known by the name Lancer and particularly characterized as to uniqueness by the combined characteristis of flat capitulum form, spooned daisy capitulum type, dark lavender pink ray floret color, diameter across face of capitulum up to 100 mm., tall plant height, semi-spreading branching pattern, average natural season flowering date of September 22 and average flowering response period of seven weeks in photoperiodic controlled short day programs.

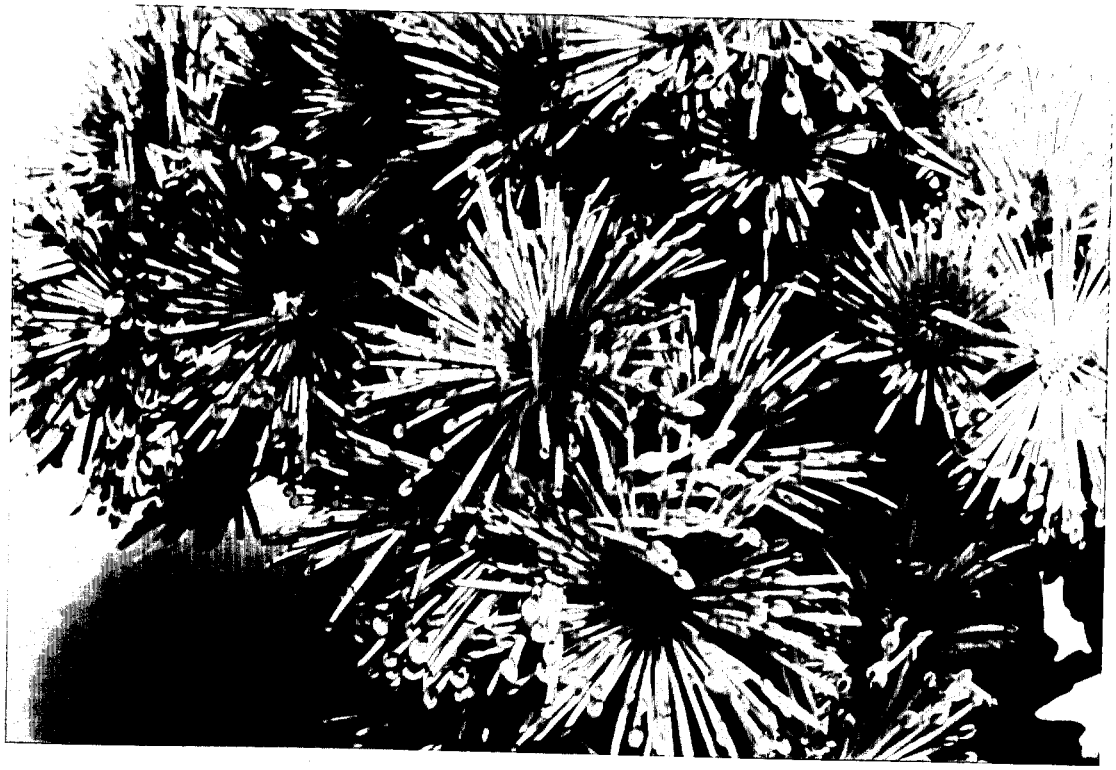

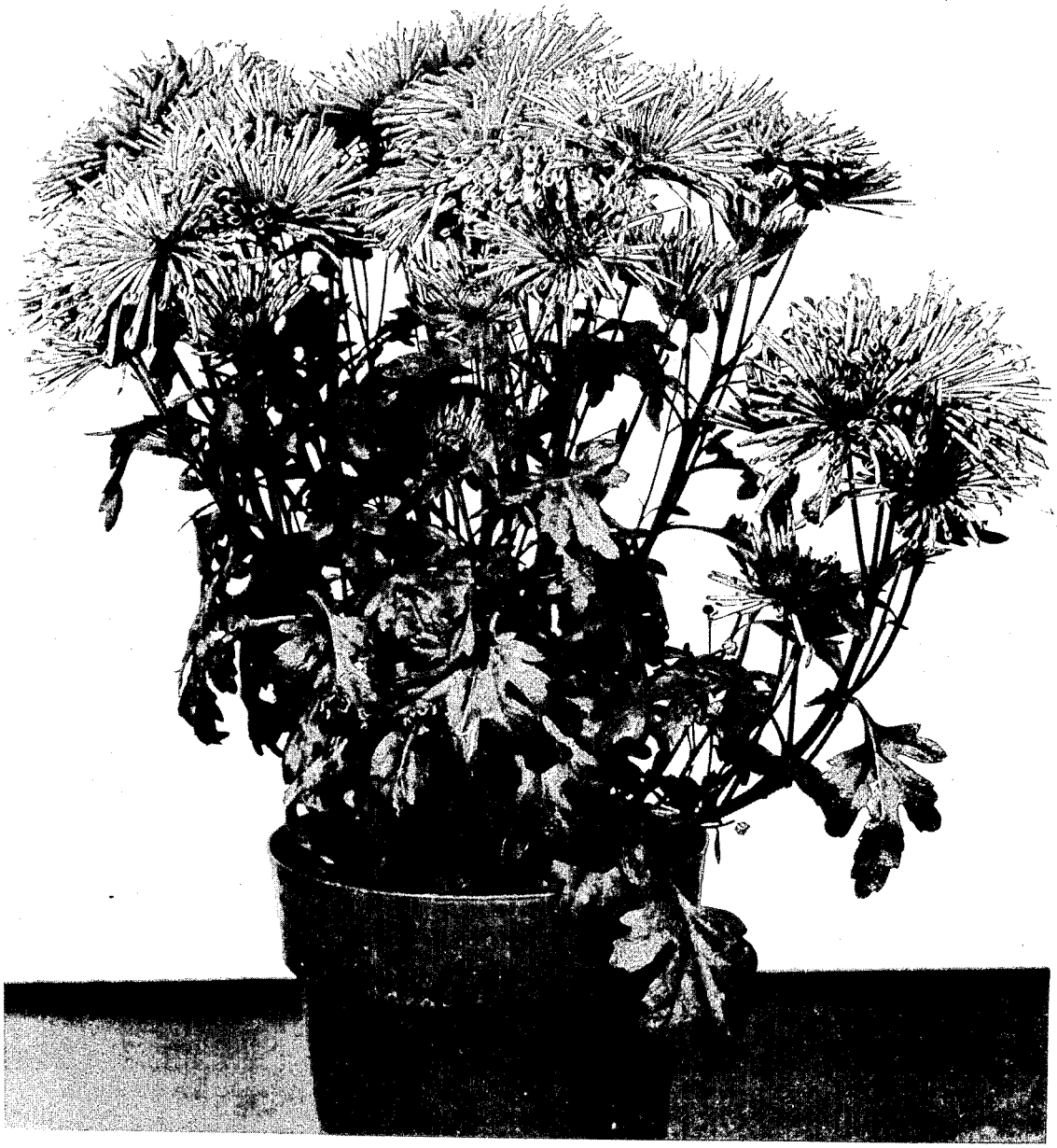

* * * * *